(12) United States Patent
Hinson

(10) Patent No.: US 10,406,255 B2
(45) Date of Patent: Sep. 10, 2019

(54) HEMOSTATIC TEXTILE

(71) Applicant: Highland Industries, Inc., Kernersville, NC (US)

(72) Inventor: Terry Hinson, Kershaw, SC (US)

(73) Assignee: Highland Industries, Inc., Kernersville, NC (US)

( * ) Notice: Subject to any disclaimer, the term of this patent is extended or adjusted under 35 U.S.C. 154(b) by 1020 days.

(21) Appl. No.: 14/288,621

(22) Filed: May 28, 2014

(65) Prior Publication Data
US 2015/0343111 A1    Dec. 3, 2015

(51) Int. Cl.
| | |
|---|---|
| *A61L 15/18* | (2006.01) |
| *D06C 5/00* | (2006.01) |
| *A61F 13/00* | (2006.01) |
| *A61L 15/42* | (2006.01) |
| *D04B 1/14* | (2006.01) |
| *D04B 1/22* | (2006.01) |

(Continued)

(52) U.S. Cl.
CPC ........ *A61L 15/18* (2013.01); *A61F 13/00012* (2013.01); *A61F 13/00987* (2013.01); *A61L 15/28* (2013.01); *A61L 15/42* (2013.01); *D04B 1/14* (2013.01); *D04B 1/22* (2013.01); *D06C 5/00* (2013.01); *D06C 19/00* (2013.01); *A61F 2013/00238* (2013.01); *A61L 2300/10* (2013.01); *A61L 2300/102* (2013.01); *A61L 2300/112* (2013.01); *A61L 2400/04* (2013.01); *D10B 2403/0114* (2013.01); *D10B 2509/022* (2013.01)

(58) Field of Classification Search
CPC .......... A61F 13/00012; A61F 13/00987; A61F 2013/00238; A61L 15/18; A61L 15/28; A61L 2400/04; D04B 1/14; D04B 1/22; D06C 19/00; D06C 5/00; D10B 2509/022
See application file for complete search history.

(56) References Cited

U.S. PATENT DOCUMENTS

| | | |
|---|---|---|
| 1,527,369 A | 2/1925 | Meyer |
| 3,328,259 A | 6/1967 | Anderson |

(Continued)

FOREIGN PATENT DOCUMENTS

| | | |
|---|---|---|
| GB | 874799 | 8/1961 |
| GB | 1506389 | 4/1978 |

OTHER PUBLICATIONS

Stewart, Martha, "Martha Stewart: Laundry tips will keep clothes looking their best," Deseret News, Published Jul. 2006, pp. 1-2.*

(Continued)

*Primary Examiner* — Rachael E Bredefeld
(74) *Attorney, Agent, or Firm* — Tuggle Duggins P.A.; Blake Hurt

(57) ABSTRACT

A hemostatic textile comprising glass fibers circular knit with bamboo-sourced rayon fibers in a tubular fashion. The knitted textile is scoured and dried to shrink the bamboo-sourced rayon relative to the glass fibers and to orient the glass fibers exteriorly of the bamboo-sourced rayon fibers such that when the hemostatic textile is administered to a wound, the glass fibers are the first to come in contact with any wound fluid, for example blood. This orientation aids in the activation of the hemostatic response which leads to faster clot times and improved overall wound-healing. A method of manufacturing and utilizing the hemostatic textile is also provided.

18 Claims, 5 Drawing Sheets

(51) Int. Cl.
*A61L 15/28* (2006.01)
*D06C 19/00* (2006.01)

(56) References Cited

U.S. PATENT DOCUMENTS

| | | |
|---|---|---|
| 3,419,006 A | 12/1968 | King |
| 4,192,299 A | 3/1980 | Sabatano |
| 4,323,061 A | 4/1982 | Usukura |
| 4,390,519 A | 6/1983 | Sawyer |
| 4,453,939 A | 6/1984 | Zimmerman et al. |
| 4,606,337 A | 8/1986 | Zimmermann et al. |
| 4,616,644 A | 10/1986 | Saferstein et al. |
| 4,718,897 A | 1/1988 | Elves |
| 5,800,372 A | 9/1998 | Bell et al. |
| 5,902,608 A | 5/1999 | Read et al. |
| 6,638,296 B2 | 10/2003 | Levinson |
| 6,762,336 B1 | 7/2004 | MacPhee et al. |
| 6,891,077 B2 | 5/2005 | Rothwell et al. |
| 6,897,348 B2 | 5/2005 | Malik |
| 7,201,024 B2 | 4/2007 | Hirayama et al. |
| 8,377,467 B2 | 2/2013 | Fischer et al. |
| 2006/0211965 A1 | 9/2006 | Horn et al. |
| 2014/0114224 A1 | 4/2014 | Kendall |

OTHER PUBLICATIONS (Erdumla, N et al.) Investigation of Regenerated Bamboo Fibre and Yarn Characteristics, Fibres & Textiles in Eastern Europe 2008; 16(69), p. 46, paragraph 2.

\* cited by examiner

HEMOSTATIC TEXTILE

FIELD OF THE INVENTION

The invention herein pertains to textiles such as fabrics used as bandages and particularly pertains to hemostatic tubular textiles that can reduce bleeding rapidly and a method of their manufacture.

DESCRIPTION OF THE PRIOR ART AND OBJECTIONS OF THE INVENTION

The use of textiles to staunch the flow of blood is well-known in the art. For example, U.S. Pat. No. 3,419,006 to King discloses a sterile transparent dressing for a wound and made from a hydrophilic polymeric gel of an insoluble polymer, and U.S. Pat. No. 4,323,061 to Usukura discloses a rigid bandage made from glass fibers and non-glass fibers. In addition, various methods have been attempted to quickly arrest bleeding in an injured person. Several of these methods include articles such as bandages supplemented with substances that chemically accelerate the body's natural clotting processes. Examples of such articles include the following:

U.S. Pat. No. 3,328,259 to Anderson discloses a bandage or wound dressing that incorporates polymers such as sodium carboxymethyl cellulose, hydroxyethyl cellulose, polyoxyethylene, polyvinylpyrrolidone, and the like.

U.S. Pat. No. 4,192,299 to Sabatano discloses a bandage that includes a packet containing an antiseptic substance.

U.S. Pat. No. 4,390,519 to Sawyer discloses a bandage in the form of a sponge and containing collagen or a collagen-like substance.

U.S. Pat. No. 4,453,939 to Zimmerman et al. discloses a composition useful as a wound dressing and made from a combination of collagen, fibrinogen and thrombin.

U.S. Pat. No. 4,606,337 to Zimmerman et al. discloses a resorptive sheet for closing and treating wounds, and composed of a glycoprotein matrix that contains fibrinogen and thrombin.

U.S. Pat. No. 4,616,644 to Saferstein et al. discloses an adhesive bandage that includes high molecular weight polyethylene oxide as a hemostatic agent.

U.S. Pat. No. 5,800,372 to Bell et al. discloses a dressing made from an absorbent polymer and includes microfibrillar collagen.

U.S. Pat. No. 5,902,608 to Read et al. discloses surgical aids such as bandages, gauzes, sutures, and the like, that contain fixed-dried blood cells that express platelet-derived growth factors.

U.S. Pat. No. 6,638,296 to Levinson discloses a bandage that includes a pad containing glucosamine or a glucosamine derivative.

U.S. Pat. No. 6,762,336 and International Patent Application Publication No. WO/99/59647 to MacPhee et al. disclose a multilayer bandage that includes a thrombin layer sandwiched between two fibrinogen layers.

U.S. Pat. No. 6,897,348 to Malik discloses an adhesive bandage that contains an antimicrobial agent and a hemostatic agent (e.g., chitosan, niacinamide, or ascorbic acid), or a single wound-healing agent that contains both antimicrobial and hemostatic activities (e.g., chitosan niacinamide ascorbate salt).

U.S. Pat. No. 6,891,077 to Rothwell et al. discloses fibrinogen bandages that include a procoagulant such as propyl gallate, gallic acid, or a derivative thereof Optional ingredients such as thrombin or an antimicrobial agent may also be included.

International Patent Application Publication No. WO 97/28832 to New Generation Medical Corporation discloses a hemostatic bandage that contains powdered fibrinogen and thrombin adhered to a fibrous matrix with a viscous, nonaqueous adhesive such as a viscous polysaccharide, glycol, or petroleum jelly.

The standard of care is frequently the application of a tourniquet to control "compressible" bleeding and then gauze to control the residual "noncompressible" bleeding. However, continued blood loss through gauze is a major contributor to morbidity and mortality. This has lead to the development of hemostatic textiles treated with thrombin or other hemostatic agents capable of activating the hemostatic system of the human body when applied to the wound. For example, see U.S. Pat. No. 8,377,467 to Fischer et al. for a hemostatic textile. However, methods of producing these textiles are difficult and expensive to perform, resulting in limited distribution and use. All of the aforementioned patent and patent application references are incorporated by reference herein in their respective entireties.

Thus, in view of the problems and disadvantages associated with prior art devices, the present invention was conceived and one of its objectives is to provide a hemostatic bandage knitted from glass and bamboo-sourced rayon fibers.

It is another objective of the present invention to provide a bandage finished by beam scouring the textile in a mixture of Rucogen FWK™, Hipozyme 2000™, and sodium carbonate.

It is still another objective of the present invention to provide a bandage finished by tumble drying for ninety minutes (90 min.) at one hundred fifty degrees Fahrenheit (150° F.) followed by a ten minute (10 min.) cool down.

It is yet another objective of the present invention to provide a knitted textile bandage with a loop length of 0.1092 inches (0.2774 centimeters).

It is still yet another objective of the present invention to provide a method of manufacturing a knitted hemostatic bandage which exhibits advantageous absorptive and coagulative properties.

It is a further objective of the present invention to provide a knitted hemostatic textile knitted in a tubular shape, resulting in a two-ply bandage.

It is another further objective of the present invention to provide a knitted tubular shaped hemostatic textile which can be divided to provide a single ply bandage for coverage of larger wounds/areas without decreasing effectiveness.

It is still a further objective of the present invention to provide a method of knitting a tubular hemostatic bandage from fiberglass and bamboo-sourced rayon fibers.

It is yet a further objective of the present invention to provide a method of finishing a tubular knit hemostatic bandage including the finishing steps of beam scouring and tumble drying the textile with exceedingly low fall out rate.

It is yet still a further objective of the present invention to provide a knitted hemostatic textile bandage which may incorporate a radiopaque fiber knitted in various positions for detection and removal of the bandage following wound administration.

It is yet another further objective of the present invention to provide a method of knitting a tubular textile in either a relaxed or taut configuration, with each configuration providing beneficial hemostatic qualities.

Various other objectives and advantages of the present invention will become apparent to those skilled in the art as a more detailed description is set forth below.

SUMMARY OF THE INVENTION

The aforesaid and other objectives are realized by providing a circular knit two-ply textile formed from bamboo-sourced rayon and glass fibers knit into a "relaxed" fabric and used as a hemostatic bandage. The composition of the textile is comprised of sixty-five percent (65%) fiberglass fibers and thirty-five percent (35%) bamboo-sourced rayon fibers, with the fibers oriented after finishing such that when the textile is used as a bandage and comes in contact with a fluid such as blood, the fiberglass fibers are positioned exteriorly of the rayon fibers on the textile face, allowing the fiberglass to stimulate the body's natural clotting cascade, resulting in faster hemostatic response, cessation of bleeding, increased wound healing and overall patient health.

A method of manufacturing a hemostatic bandage as described above is also provided and includes the step of knitting a tubular fabric comprised of sixty-five percent (65%) glass fibers and thirty-five percent (35%) bamboo-sourced rayon fibers on a circular knit machine configured to half-gauge knit the textile, resulting in an extra-long carry-over loop. The method also includes the steps of preparing, scouring, and drying the fabric which results in a smaller overall size, with the bamboo-sourced fabrics shrinking more due to their vegetative-based cellulous which pushes the glass fibers to loop and become positioned more exteriorly on the textile face as a result. This positioning causes the looped glass fibers to contact fluid such as blood first when the hemostatic bandage is in use, allowing the glass to stimulate the body's natural clotting cascade as indicated above.

DETAILED DESCRIPTION OF THE PREFERRED EMBODIMENT AND OPERATION OF THE INVENTION

Figure 1:
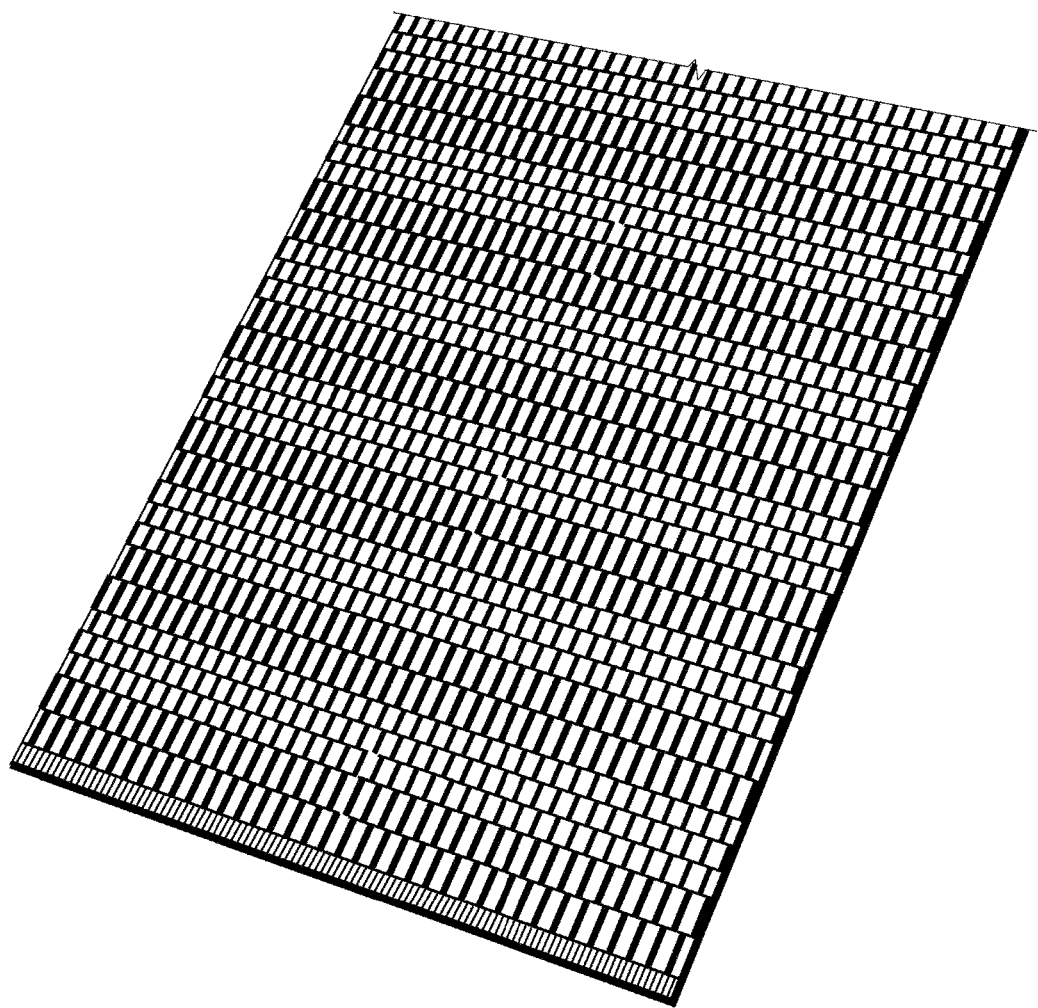
FIG. 1 shows a prior art hemostatic bandage.

As described above, hemostatic bandages incorporating secondary fibers are known in the art. For example, FIG. 1 illustrates the prior art hemostatic bandage described in U.S. Pat. No. 8,377,467 (the '467 patent, currently licensed by the instant assignee) which is either woven or knitted and sold under the trade names Stasilon™ and NuStat™. The hemostatic bandage taught by the '467 displays hemostatic properties and fluid absorbency. To further enhance the hemostatic properties of the hemostatic textile made from the composite formed from glass and secondary fibers, additional blood factors such as thrombin, lyophilized blood cells, lyophilized platelets, fibrin, fibrinogen, or combinations of these, may be added. These additional factors aid in activating the body's natural hemostasis cascade and result in a material that can arrest bleeding. The combination of glass fibers, secondary fibers, and additional blood factors produced a hemostatic textile that arrests bleeding, and is useful in situations where large hemorrhages exist or when a patient cannot be immediately admitted to a hospital or trauma treatment center. However the '467 bandage has experienced inconsistent performance due to its manufacture and use. For example, an embodiment of the '467 bandage consists of a hemostatic layer designed to accelerate hemostasis, and an outer layer designed for surface texture, moisture transfer, fluid adsorption and microbial protection. In practice, a bandage with a single side of hemostatic-activation inherently leads to user error, particular in emergency and combat environments where speed may trump attention to detail.

Figure 2:
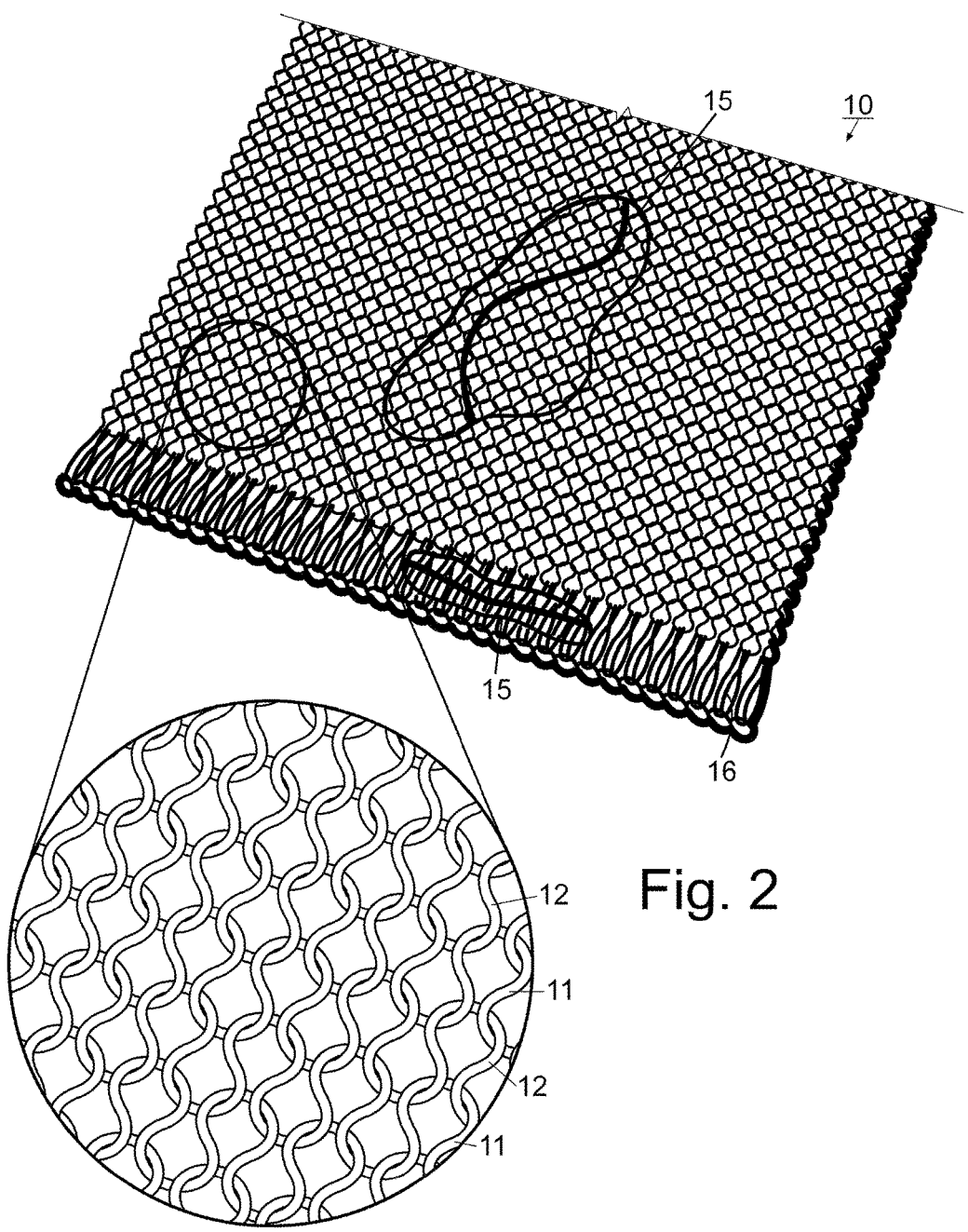
FIG. 2 pictures an embodiment of the tubular knit hemostatic bandage of the present invention.
Figure 3:
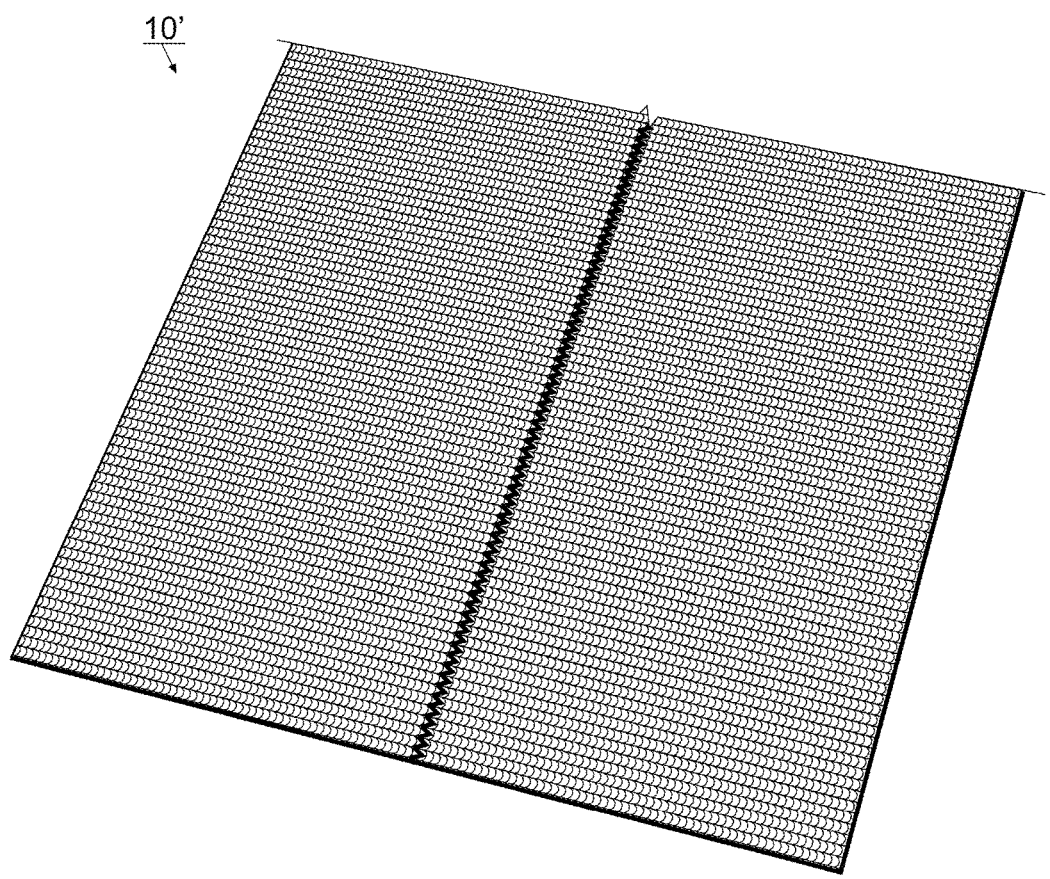
FIG. 3 depicts an alternative embodiment of the knit hemostatic bandage of the present invention.

For a better understanding of the invention and its operation, turning now to the drawings, FIGS. 2 and 3 illustrate respective side perspective views of two embodiments of hemostatic bandages 10 and 10'. FIG. 2 shows a tubular, two-ply embodiment of hemostatic bandage 10 as produced by the method discussed in further detail below. Hemostatic bandage 10 is knitted in what is recognized in the art as a "relaxed" configuration, in that the stitches are not pulled tight upon knitting, resulting in a bandage with greater spaced openings therebetween, and thus less overall material per unit surface area compared to hemostatic bandage 10' (FIG. 3), which is more tightly knit. This "relaxed" or loose configuration also permits a higher volume of fluid such as blood to interact with the pile fibers of hemostatic bandage 10, leading to an increased hemostatic response when bandage 10 is applied to a wound, and correspondingly to a reduced time to effective clot formation.

Figure 4:
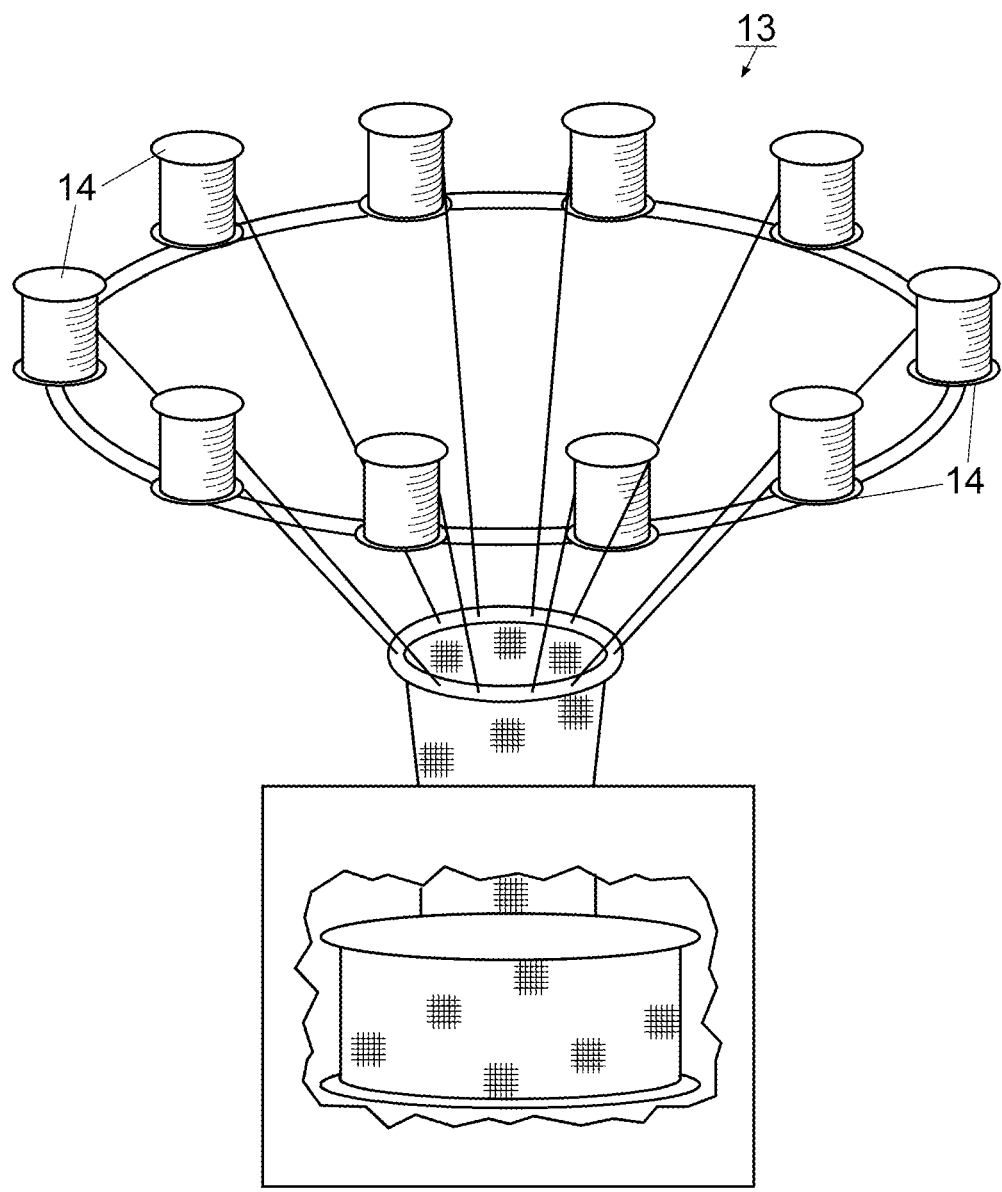
FIG. 4 demonstrates schematically the circular knitting machine for producing the bandages of FIGS. 2 and 3.

In a preferred embodiment of hemostatic bandage 10, primary fibers 11 and secondary fibers 12 are knitted in a relaxed, knit stitch or purl stitch pattern on circular knitting machine 13 as shown schematically in greater detail in FIG. 4. By comparison, hemostatic bandage 10' may be formed on the same circular knitting machine, but may be knitted in a comparatively tighter knit stitch pattern. While the patterns indicated above are preferred, other knit patterns resulting in an absorbent textile comprised of fibers capable of assisting in the activation of the hemostatic cascade are also contemplated within the scope of the instant invention. Preferably primary fibers 11 are formed from glass fibers, such as a fiberglass prepared by extrusion or electrospinning processes, and has fiber diameters from five nanometers (5 nm) to fifteen micrometers (15µ). The types of glass contemplated for use in the present invention include but are not limited to alumino-borosilicate glasses with low sodium oxide content, borosilicate glass, lead glass, aluminosilicate, alkali-barium silicate, vitreous silica, chalcogenide glass, phosphate glass, and bioactive glass sold under the trade name BIOGLASS™. The dimensions of the glass fiber component may be described by conventional nomenclature, including the following designations: B (3.5 micron diameter); C (4.5 micron diameter); D (5 micron diameter); DE (6 micron diameter); E (7 micron diameter); G (9 micron diameter); H (10 micron diameter); or K (13 micron diameter). In addition, strand count of the glass fiber component can range from 900 to 37. The grade of the glass fiber may be any of electrical grade ("E"), chemical grade ("C"), or high strength ("S"), and the filaments may be in any arrangement, for example continuous, staple, or textured. The fiberglass fibers may also be used singly or in a plied state using 2 to 20 or more fibers. Fiberglass material is available commercially from various suppliers such as Owens Corning, and is available commercially as Grades G75, E-grade fiberglass, and the like, using the designations described above.

Preferred secondary fibers 12 are formed from any other fiber that can be combined with primary fibers 11 to impart absorbency, softness, and additional hemostatic activity to bandage 10. Examples of useful secondary fibers 12 include, but are not limited to, silk fibers; polyester fibers; nylon fibers; ceramic fibers; polysaccharide fibers including plant fibers such as raw or regenerated (e.g., chemically processed), cotton, rayon, linen, ramie, jute, sisal, flax, soybean, corn, hemp, and lyocel; animal fibers such as wool; lactide and/or glycolide polymers; lactide/glycolide copolymers; silicate fibers; polyamide fibers; feldspar fibers; zeolite fibers, zeolite-containing fibers; acetate fibers; plant fibers that have been genetically engineered to express mammalian coagulation proteins or mammalian vasoactive factors. Other secondary fibers 12 that are suitable for use in the present invention are fibers that have been covalently modified with polymers to promote water absorbency (e.g., polyvinyl alcohols) and polymers that contain molecular moieties that activate hemostatic systems (e.g., linear or cyclized-arginine-glycine-aspartate-moieties such as those found in eptifibatide). Preferred secondary fibers 12 include plant-sourced rayon fibers such as raw or regenerated (e.g., chemically processed) bamboo fibers, cotton fibers, and the like, that have high moisture absorbency and that are capable of activating the intrinsic coagulation cascade. Secondary fibers 12 may be prepared using conventional methods, including ring, open end (OE), rotor, or air jet spinning, and may have counts ranging from 1/1 to 100/1 Ne.

Preferred hemostatic bandages 10 and 10' are knit on circular knitting machine 13, for example a fifteen inch (38.1 cm) Vanguard™ machine with sixteen needles per inch and totaling seven hundred sixty (760) total needles capable of producing a jersey knit construction textile revolving clockwise to produce one hundred fifty yards (450 feet) of tubular knitted textile. Circular knitting machine 13 may include one or more pairs of primary fiber 11 and secondary fiber 12 loaded onto carriers 14 that knit the respective fibers as is known in the art, preferably alternating between one complete stitch of primary fiber 11 followed by one complete stitch of secondary fiber 12. Each rotation of circular knitting machine 13 may produce eighty-three inches (210.8 cm) of knitted textile with each stitch forming a loop 0.1092 inches (0.2774 cm) in length per needle. While circular knitting machine 13 may be configured with any number of engaged carriers 14 loaded with primary fibers 11 or secondary fibers 12, knitting machine 13 is preferably configured in what is known as a "half-gauge" configuration, which means that every other needle in knitting machine 13 engages fibers from respective carriers 14, resulting in a carryover loop 16 that is substantially larger (approximately twenty percent (20%) or 0.0254 inches (0.0645 cm)) than that which is formed when all needles are engaged.

After hemostatic bandages 10, 10' are circular knit as described above, bandages 10, 10' are subjected to a finishing process to orient looped primary fibers 11 exteriorly of secondary fibers 12 such that when the face of bandages 10, 10' are administered to a wound, the glass in primary fibers 11 is the first material to interact with wound fluid such as blood, stimulating the activation of the hemostatic response. The finishing process includes scouring and tumble drying the textile after knitting is complete. In the case of bandage 10', after the finishing process the resulting tubular structure of hemostatic bandage 10' may be divided into specified lengths and widths as desired.

The various components of a given scouring process are known in the art, but for clarity, in a beam scouring process textile may be wrapped around a drum referred to as a beam and placed in a large vat containing scouring fluids such as water or aqueous chemicals. The vat includes a pump that draws the scouring fluid from the vat reservoir and pumps it into the beam, where it flows through the wrapped fabric and returns to the reservoir. Prior to use, bleach and water are added to the vat and are warmed to one hundred twenty degrees (120°). Once warm, an empty beam is inserted and the fluids are pumped through the vat for ten (10) minutes to ensure that the vat and beam are properly sterile before disposing of the water and bleach.

Preferably, hemostatic bandages 10, 10' are beam scoured after being knit, wrapping bandages 10, 10' under tension around a drum atop five (5) layers (about fifteen (15) yards of material, depending on the size of the beam) of filtering material and placed into the vat. A scouring liquid is introduced into the center of the textile and is pumped through the layers of textile in a direction away from the beam center. While other scouring methods are known in the art, beam scouring is preferred because it results in substantially less trauma on the comparatively delicate glass components of primary fibers 11 than other scouring methods. The scouring liquid may be comprised of any number of known chemicals, but preferably is made up of Rucogen FWK™, Hipozyme 2000™, and sodium carbonate. The detergent mixture commercially available under the trade name Rucogen FWK™ from Rudolf-Venture Chemicals, Inc. is comprised of nonionic surfactants, propan-2-ol, (2-methoxymethylethoxy)propanol, and (R)-p-mentha-1,8-diene. The alpha-amylase mixture commercially available from Dystar L.P. under the trade name Hipozyme 2000™ is comprised of proprietary enzymes in an inert vehicle solution. Sodium carbonate ($Na_2CO_3$) is commercially available from several manufacturers and is also known in the textile industry as soda ash. The scouring process is essential to the proper production of hemostatic bandages 10 and 10' as the scouring liquid breaks down and removes the undesirable starch and paraffin surrounding primary fibers 11 as well as "de-sizing" the textile, which along with the tumble dry process causes the loops of primary fibers 11, by the significant shrinking of secondary fibers 12, to be positioned more exteriorly (that is to say, to increase the surface area of primary fibers 11 exposed to the exterior of tubular hemostatic bandage 10 compared to other fibers) relative to secondary fibers 12.

Hemostatic bandages 10, 10' are also preferably tumble dried after the knitting and beam scouring processes. Like the scouring process described above, there are many known methods of drying textiles, but the tumble drying process as discussed herein is superior for several reasons. The tumbling process, coupled with the appropriate temporal and temperature variables, results in a textile with a surprisingly low fall out rate (generally defined as the percentage of fractured primary fibers that fracture and "fall out" of the resulting textile due to breakage) but otherwise protecting the structural integrity of hemostatic bandages 10, 10'. From manufacturing efficiency and quality control standpoints, this also results in a more consistent textile, as it is less likely that primary fibers 11 and secondary fibers 12 which contain otherwise undetectable structural defects will survive the process. Therefore, it is preferable to tumble dry hemostatic bandages 10, 10' for approximately ninety (90) minutes at one hundred fifty degrees Fahrenheit (150° F.) followed by a ten (10) minute cool down prior to removal. Preferred hemostatic bandages 10, 10' can undergo this process with a very low fall out rate. Following this drying step, the textile is de-sized as described above, leading to the proper orientation of the loops of primary fibers 11 positioned exteriorly of secondary fibers 12. For example, a prior art hemostatic bandage sold under the trade name Quick Clot™ was compared to hemostatic textile 10, 10' in terms of primary fiber 11 surface area as it related to size and weight of a given bandage. The instant bandage defined a fiber-exposed surface area of one hundred and ninety-three squared centimeters (193 cm$^2$) in one square inch (1") of fabric, compared to only twenty-one centimeters squared (21 cm$^2$) for the prior art bandage. Similarly, textiles 10, 10' defined a fiber-exposed surface area of seven hundred centimeters squared (700 cm$^2$) in one gram (1 g) of bandage, compared to only five hundred forty centimeters squared (540 cm$^2$) in the prior art bandage. This substantial increase in fiber-exposed surface area is responsible for the increased performance of hemostatic textile 10, 10' over the prior art.

The mechanical devices of the finishing process, such as the beam scouring and drying machines, are provided here as examples and are not intended to limit the scope of the instant invention in any way. It is understood that one of ordinary skill in the art may be aware of many machines for scouring and drying a textile, but it is only by following the disclosed methods that a structurally sound and consistently performing hemostatic bandage results, a bandage with primary fibers 11 being oriented exteriorly of secondary fibers 12.

Although not shown in FIG. 3, both hemostatic bandages 10 and 10' may further incorporate radiopaque fiber 15, shown in lateral and longitudinal positions in FIG. 2. Although two radiopaque fibers 15 are illustrated knitted into hemostatic bandage 10, it should be understood that one or more fibers 15 may be included in a variety of positions throughout bandages 10, 10'. Radiopaque fiber 15 is vital to the detection and removal of bandages 10, 10' following administration to a wound. As would be understood, after hemostatic bandages 10, 10' have stopped the bleed, eventually they must be removed and the wound properly cleaned. During this removal process (and although primary fibers 11 are designed to reduce adherence), it is common that small pieces of bandages 10, 10' may remain in or around the wound. Failing to remove foreign objects from a wound often leads to dangerous infection, which is why, with the inclusion of radiopaque fiber 15, a medical professional may x-ray the wound following treatment. While bandages 10, 10' would not show up on such an image, radiopaque fiber 15, by virtue of its more reflective nature compared to knitted textile, may be visible and thus easily removable.

Figure 5:
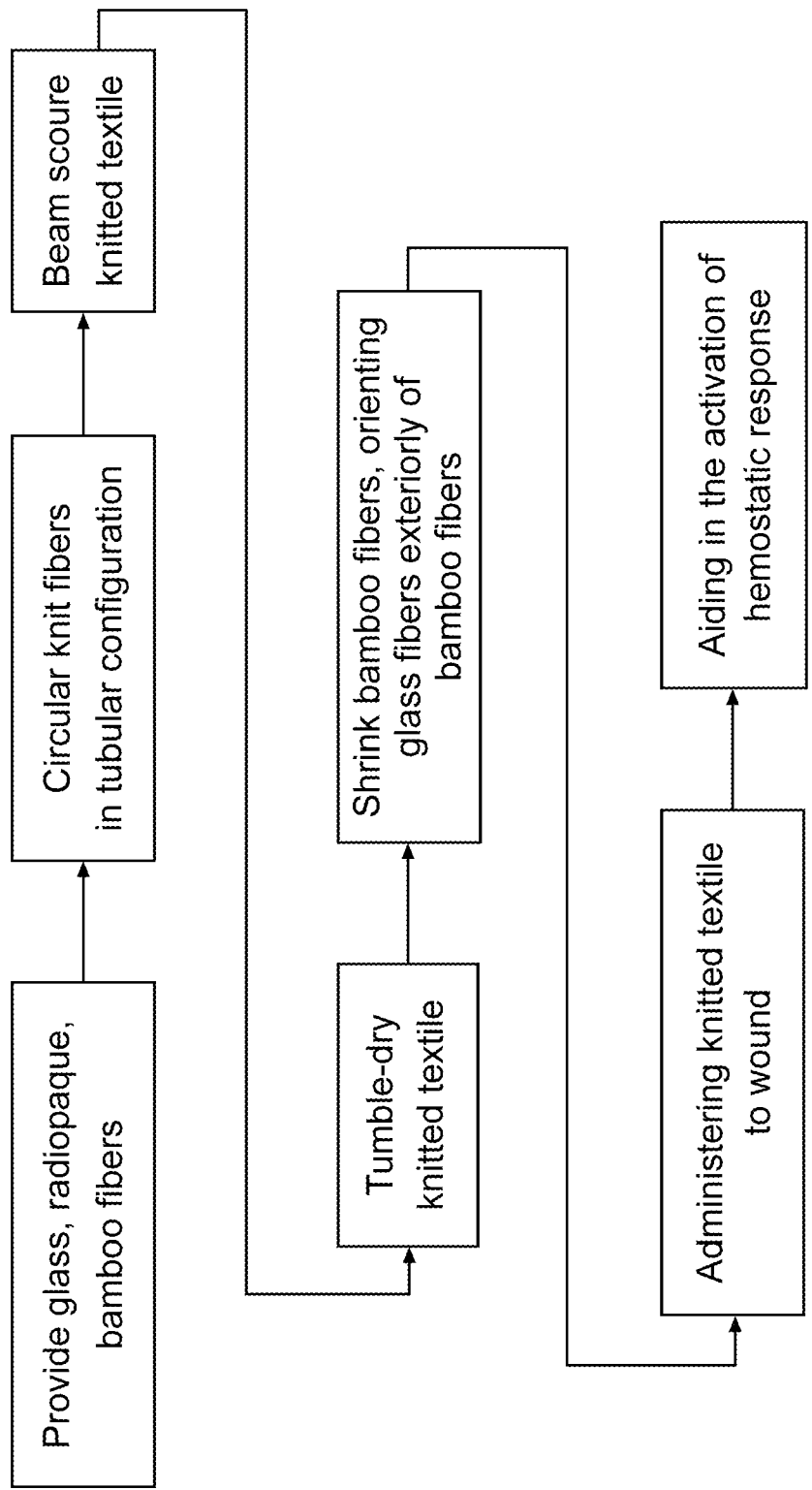
FIG. 5 illustrates a schematic method of forming the hemostatic bandages of FIGS. 2 and 3.

A method of manufacturing tubular hemostatic bandages 10 or 10' is represented schematically in FIG. 5 and includes the steps of providing primary fibers 11 such as fiberglass fibers, secondary fibers 12 such as bamboo-sourced rayon fibers, and radiopaque fibers 15, knit stitching the respective fibers 11, 12, and 15 on circular knit machine 13 as schematically illustrated in FIG. 4 in a tubular configuration with 0.1092 inch (0.2774 centimeter) loops, and collecting knitted hemostatic bandages 10, 10', for example on a roll in the base of knit machine 13. Hemostatic bandage 10 may be sewn, melted, or otherwise attached at opposing ends during finishing to create a two-ply textile or the ends may be left unsecured to form a tubular bandage. Hemostatic bandage 10' results from the same knitting process, but whereas hemostatic bandage 10 is knitted in a "relaxed" configuration, hemostatic bandage 10' is knitted under greater tension than hemostatic bandage 10, resulting in a tighter knit pattern. Hemostatic bandage 10' is also cut along one side, resulting in a single-ply bandage instead of the tubular structure defined by hemostatic bandage 10.

Hemostatic bandages 10, 10' are prepared for scouring by turning the textile "inside out" such that the exterior faces are oriented towards the inside of the tubular structure defined by hemostatic bandage 10, for example by loading tubular hemostatic bandage 10, 10' onto a turnpipe (not shown) and passing bandages 10, 10' over an end, similar to the removal of a sock, until the entire length of bandages 10, 10' has passed the end point and is entirely inside out. The inside out textile is wrapped in a spiral pattern around a central beam atop approximately five (5) layers (roughly fifteen (15) yards depending on the size and diameter of the beam) of filter fabric (for example a polyester substrate fabric) and placed in a large vat for scouring. Preferably, the spiral pattern defined by wrapped bandages 10, 10' should be continuous throughout the length of the textile and it is preferable that eighty percent (80%) of a spiral overlap with the previous and following wraps, preventing any gaps. An additional five (5) layers (roughly fifteen (15) yards depending on the size and diameter of the beam) of filter fabric is wrapped atop hemostatic bandage 10, 10', and the opposing ends of the textile may be affixed to respective lengths of filter fabric, for example via mechanical fasteners, adhesives, or the like. Further attachments means such as string, rope, or clamps may also be utilized to ensure that the roll of textile is secure, and does not unravel during finishing.

The beam scouring machine is prepared prior to scouring hemostatic bandages 10, 10'. Specifically, the vat is filled with water (approximately twelve hundred (1200) gallons) and one (1) gallon of bleach, warmed to one hundred twenty degrees (120°) Fahrenheit, and pumped throughout for ten (10) minutes. Thereafter, the water and bleach are dumped out of the vat and the vat is again filled with approximately twelve hundred (1200) gallons of water in preparation of receipt of a beam containing the wrapped hemostatic textile. Scouring liquid comprising a mixture of 4.4 lb (1.99580642 kg) of Rucogen FWK™, 0.88 lb (399.1612856 g) of Hipozyme 2000™, and 4.4 lb (1.99580642 kg) of sodium carbonate is preferably introduced centrally via the beam and is cycled via a pump outwardly, engaging hemostatic bandages 10, 10', cleaning the textiles, breaking down any residual starch, and de-sizing hemostatic bandages 10, 10'. These reagents are preferably introduced on a temporal or temperature schedule designed to maximize their individual and combined effectiveness as well as to retain the structural integrity of hemostatic bandages 10, 10'. For example, a vat heater is set to one hundred fifty degrees (150°) Fahrenheit, but as the temperature reaches one hundred thirty five degrees (135°) Fahrenheit, the sodium carbonate is added to the vat. As the temperature reading on the vat reaches one hundred forty degrees (140°) Fahrenheit, the Rucogen FWK™ is introduced into the vat and allowed to circulate for ten (10) minutes. Thereafter, as the temperature in the vat reaches one hundred forty five degrees (145°) Fahrenheit the Hipozyme 2000™ is added to the vat. Once the temperature reaches one hundred fifty degrees (150°) Fahrenheit, the mixture is pumped in from the vat reservoir, out of the center of the beam, through the wrapped textiles, and back into the reservoir for twenty (20) minutes. Additional water may be added to the vat for five (5) minutes in an overflow condition, diluting the aforementioned mixture before the vat is emptied. Following this scouring process, hemostatic bandages 10, 10' may be rinsed, preferably twice, by filling the vat with water, warming the water to one hundred twenty degrees (120°) Fahrenheit, cycling the warmed water for ten

(10) minutes, overflowing the vat with water for an additional five (5) minutes, and then draining the tank. The beam, including the scoured textiles, is removed and hemostatic bandages 10, 10' are transported for drying.

The method also includes the step of removing the scoured textile from the beam and tumble drying hemostatic bandages 10, 10', preferably for approximately ninety (90) minutes at one hundred and fifty degrees Fahrenheit (150° F.) followed by a ten (10) minute cool down cycle, further de-sizing hemostatic bandages 10, 10' and producing a textile with superior structural stability.

After textile 10, 10' has been scoured and dried as described above, the resulting fabric and particularly secondary fibers 12 have shrunk considerably which causes the formation and protrusion of loops of primary fibers 11. Textile 10, 10' is again turned "inside out", returning the textile face to its original exteriorly oriented configuration.

Thereafter the processed textile is removed and readied for packaging in various sizes and shapes for tending to different sized wounds. Further hemostatic bandages 10, 10' may come in a roll of indeterminate length for cutting to size during application. As would be understood due to the knitting, beam scouring and drying processes, either side of hemostatic bandages 10, 10' may be administered to a wound, aiding in the activation of the hemostatic response and reducing clotting time.

The illustrations and examples provided herein are for explanatory purposes and are not intended to limit the scope of the appended claims. Although many beam scouring machines and drying machines are known in the art, the provided examples were given in view of a Morton™ beam dye machine with a rectangular vat with 1200 gallon capacity and either a Fabcon™ or Milnor™ industrial dryer.

I claim:

1. A method of manufacturing a hemostatic textile comprising the steps of:
    circular knitting glass fibers alternating stitches with secondary fibers to form the hemostatic textile;
    beam scouring the hemostatic textile, wherein the beam scouring comprises: wrapping a first filter fabric in a spiral pattern about a central beam; wrapping the hemostatic textile in a spiral pattern atop the first filter fabric, with about 80% of each wrap overlapping the previous wrap; wrapping a second filter fabric in a spiral pattern atop the hemostatic textile; preparing a beam scouring machine by heating water to 120 degrees F. and pumped throughout for 10 minutes before discarding the water; filling the beam scouring machine with water and heating to 150 degrees F.; adding sodium carbonate as the water reaches 135 F degrees; introducing a detergent as the water reaches 140 degrees F. and is allowed to circulate for 10 minutes before adding an enzyme mixture to form a scouring mixture; urging the scouring mixture through the hemostatic textile via the beam scouring machine for about 20 minutes: and rinsing the hemostatic textile by warming water to 120 degrees F. and cycling the warmed water through the hemostatic textile via the beam scouring machine;
    tumble drying the hemostatic textile; and
    configuring the glass fibers to be oriented exteriorly of the secondary fibers in the hemostatic textile to aid in the activation of a hemostatic response.

2. The method of claim 1 wherein the secondary fibers are comprised of bamboo-sourced rayon.

3. The method of claim 2 wherein the relative amounts of the fibers as based on the total weight of the textile are sixty-five percent (65%) glass fibers and thirty-five percent (35%) bamboo-sourced rayon fibers.

4. The method of claim 1 further comprising the step of shrinking the secondary fibers relative to the glass fibers.

5. The method of claim 1 wherein circular knitting further includes the step of half-gauge knitting.

6. The method of claim 1 further comprising the step of knitting a radiopaque fiber among the glass and secondary fibers.

7. The method of claim 5, wherein the step of half-gauge knitting produces a carryover loop in the hemostatic textile that is approximately 20% larger than a carryover loop formed during full-gauge knitting.

8. The method of claim 1 further comprising the step of turning the textile inside out prior to scouring, such that one or more exterior faces are oriented towards an interior portion of a tubular structure formed during knitting.

9. The method of claim 1 wherein the step of tumble drying the hemostatic textile includes tumble drying the hemostatic textile in an industrial dryer for approximately 90 minutes at 150 degrees F. to de-size the hemostatic textile.

10. A method of manufacturing a two-ply, hemostatic textile comprising the steps of:
    circular knitting glass fibers alternating stitches with secondary fibers to form the hemostatic textile with a tubular structure, wherein the relative amounts of the fibers as based on the total weight of the textile are sixty-five percent (65%) glass fibers and thirty-five percent (35%) bamboo-sourced rayon fibers;
    turning the hemostatic textile inside out prior to scouring, such that one or more exterior faces are oriented towards an interior portion of the tubular structure;
    beam scouring the hemostatic textile by wrapping a first filter fabric in a spiral pattern about a central beam, wrapping the hemostatic textile in a spiral pattern atop the first filter fabric, with 80% of each wrap overlapping the previous wrap, wrapping a second filter fabric in a spiral pattern atop the hemostatic textile, preparing a beam scouring machine by water to 120 degrees F. and pumped throughout for 10 minutes before discarding the water, filling the beam scouring machine with water and heating to 150 degrees F., adding sodium carbonate as the water reaches 135 F degrees, introducing a detergent defined as a mixture of propan-2-ol, (2-methoxymethylethoxy)propanol, and (R)-p-mentha-1,8-diene as the water reaches 140 degrees F. and is allowed to circulate for 10 minutes before adding an enzyme mixture defined as an alpha-amalyse enzyme mixture, urging the scouring mixture through the hemostatic textile via the beam scouring machine for 20 minutes, and rinsing the hemostatic textile by warming water to 120 degrees F. and cycling the warmed water through the hemostatic textile via the beam scouring machine; and
    tumble drying the hemostatic textile in an industrial dryer for approximately 90 minutes at 150 degrees F. to de-size the hemostatic textile, and configuring the glass fibers to be oriented exteriorly of the bamboo-sourced rayon fibers to aid in the activation of a hemostatic response.

11. A method of manufacturing a hemostatic textile comprising the steps of:
    knitting glass fibers alternating stitches with secondary fibers in a relaxed configuration to form the hemostatic textile;
    beam scouring the hemostatic textile, wherein the beam scouring comprises: wrapping a first filter fabric about a central beam; wrapping the hemostatic textile atop the first filter fabric; wrapping a second filter fabric atop the hemostatic textile; preparing a beam scouring machine by heating water and pumping the water throughout before discarding the water; filling the beam scouring machine with water and heating the water; adding sodium carbonate as the water reaches a first predetermined temperature; introducing a detergent as the water reaches a second predetermined temperature and allowing the water to circulate for a predetermined amount of time before adding an enzyme mixture to form a scouring mixture; urging the scouring mixture through the hemostatic textile via the beam scouring machine; and rinsing the hemostatic textile by warming water to a third predetermined temperature and cycling the water through the hemostatic textile via the beam scouring machine;

tumble drying the hemostatic textile; and configuring the glass fibers to be oriented exteriorly of the secondary fibers in the hemostatic textile to aid in the activation of a hemostatic response.

12. The method of claim 11 wherein the secondary fibers are comprised of bamboo-sourced rayon.

13. The method of claim 12 wherein the relative amounts of the fibers as based on the total weight of the textile are sixty-five percent (65%) glass fibers and thirty-five percent (35%) bamboo-sourced rayon fibers.

14. The method of claim 11 further comprising the step of shrinking the secondary fibers relative to the glass fibers.

15. The method of claim 11 wherein the step of knitting the glass fibers and secondary fibers is defined by circular knitting, and wherein circular knitting further includes the step of half-gauge knitting.

16. The method of claim 15, wherein the half-gauge knitting produces a carryover loop in the hemostatic textile that is approximately 20% larger than a carryover loop formed during full-gauge knitting.

17. The method of claim 15 further comprising the step of turning the textile inside out prior to scouring, such that one or more exterior faces are oriented towards an interior portion of a tubular structure formed during knitting.

18. The method of claim 11 further comprising the step of knitting a radiopaque fiber among the glass and secondary fibers.

* * * * *